(12) United States Patent
Che et al.

(10) Patent No.: US 7,541,379 B2
(45) Date of Patent: Jun. 2, 2009

(54) DI(AMIDO-SUBSTITUTED)HETEROARENE COMPOUNDS AS OSTEOBLASTOGENESIS AGENTS

(75) Inventors: Chi Ming Che, Hong Kong (HK); Annie Wai-Chee Kung, Happy Valley (HK)

(73) Assignee: The University of Hong Kong, Hong Kong (CN)

( * ) Notice: Subject to any disclaimer, the term of this patent is extended or adjusted under 35 U.S.C. 154(b) by 281 days.

(21) Appl. No.: 11/580,170

(22) Filed: Oct. 10, 2006

(65) Prior Publication Data

US 2007/0149609 A1 Jun. 28, 2007

Related U.S. Application Data

(60) Provisional application No. 60/725,283, filed on Oct. 12, 2005.

(51) Int. Cl.
*A61K 31/40* (2006.01)
*A61K 31/38* (2006.01)
*A61K 31/34* (2006.01)

(52) U.S. Cl. .................. 514/426; 514/447; 514/472

(58) Field of Classification Search .................. 514/426, 514/447, 472
See application file for complete search history.

(56) References Cited

OTHER PUBLICATIONS

Lane, N.E.; *Epidemiology, Etiology, and Diagnosis of Osteoporosis*; Am J. Obstetrics and Gynecology (2006), vol. 194, pp. S3-11.
Ling, H. et al.; *Ruthenium(II) Porphyrin-Catalyzed Amidation of Aromatic Heterocycles*; Organic Letters (2004), vol. 6, No. 14, pp. 2405-2408.
Li, Z.Y. et al.; *Unusual Metalloporphycenes. First Syntheses of Carbonyl-and Dioxo-Containing Osmium and Ruthenium Tetrapropylporphycene Complexes*; Inorg. Chem. (1992), vol. 31, No. 12, pp. 2670-2672.
Mosmann, T.; *Rapid Colorimetric Assay for Cellular Growth and Survival: Application to Proliferation and Cytotoxicity Assays*; J. Immunol. Methods (1983), vol. 65, pp. 55-63.
Nakashima, K. et al.; *The Novel Zinc Finger-Containing Transcription Factor Osterix is Required for Osteoblast Differentiation and Bone Formation*; Cell (2002), vol. 108, pp. 17-29.
Cheung, W.M.W. et al.; *Dimethyl Sulfoxide as an Inducer of differentiation in Preosteoblast MC3T3-E1 Cells*; FEBS. Letters (2006), 580, pp. 121-126.
C.H. III: Osteoporosis: A world-wide problem, *Osteoporosis* 1990: Denmark, Osteopress ApS (1990), 33.

*Primary Examiner*—Raymond J Henley, III
(74) *Attorney, Agent, or Firm*—Robert D. Katz; Cooper & Dunham LLP

(57) ABSTRACT

The present invention relates to di(amido-substituted)-heteroarene compounds and their use as osteoblastogenesis agents. The invention provides a method for inducing osteogenesis in a precursor cell capable of undergoing osteogenesis.

21 Claims, 7 Drawing Sheets

DI(AMIDO-SUBSTITUTED)HETEROARENE COMPOUNDS AS OSTEOBLASTOGENESIS AGENTS

CROSS REFERENCE TO RELATED APPLICATION

This application claims the benefit of U.S. Provisional Application Ser. No. 60/725,283, filed Oct. 12, 2005, the entire contents of which are incorporated by reference.

FIELD OF THE INVENTION

The invention is directed to the use of novel di(amido-substituted)heteroarene compounds as osteoblastogenesis agents.

BACKGROUND OF THE INVENTION

Osteoporosis, characterized by decreased bone strength and increased fracture risk, is a major public health problem worldwide (Chestnut in III: Osteoporosis: A world-wide problem, *Osteoporosis* 1990: Denmark, Osteopress ApS (1990), 33). Globally, one-third of postmenopausal women and one-tenth of the elderly suffer from low bone mass and osteoporosis. Within this population, 10% of suffers die within the first year of bone fracture. It is estimated that the number of hip fractures will increase to more than 4.5 million worldwide by the year 2050 (International Osteoporosis Foundation. "Facts and Statistics about Osteoporosis and its Impact," International Osteoporosis Foundation Web site, accessed Sep. 25, 2006). Thus, the projected economic burden of osteoporosis is greater than other major health threats including cardiovascular diseases and diabetes (Lane N E. *Am J Obstet Gynecol*. (2006), 194, S3).

SUMMARY OF THE INVENTION

The present invention provides methods for modulating osteoblastogenesis. Within certain aspect, the present invention provides modulating agents capable of enhancing osteoblastogenesis.

In one such aspect, the modulating agent comprises novel bioactive small di(amido-substituted)heteroarene compounds that could notably modulate osteoblastogenic differentiation.

In another such aspect, the present invention provides methods for enhancing osteoblast differentiation in a cell, comprising contacting the cell with an osteoblastogenesis modulating agent as described above.

Within other aspects, the present invention provides methods for enhancing osteoblast differentiation in a committed immature preosteoblast MC3T3-E1 (clone 4) cell with an osteoblastogenic modulating agent as described above, wherein the step of direct contact is performed under conditions and for sufficient time to allow the drug to mediate its osteoblastogenic actions. Within related aspects, cells can be originated from any member of the kingdom Animalia including but not limited to MC3T3-E1 (clone 4) cells.

In other aspects, the present invention provides methods for treating osteoporosis in an animal, comprising administering to an animal with an osteoblastogenesis modulating agent as describe above. Within other aspects, the animal comprises any member of kingdom Animalia. Non-limiting examples of animals including a cow, monkey, horse, sheep, pig, cat, dog, mouse, rat, rabbit, guinea pig and most preferably a human. Within the same aspects, the present invention also provides methods for treating osteoporosis in human with a composition comprising an effective amount of one or more osteoblastogenesis modulating agents described above.

In another such aspect, the present invention provides pharmaceutical compositions of the modulating agent comprising the novel di(amido-substituted)heteroarene compounds. Within such embodiment, the di(amido-substituted)heteroarenes were prepared in product yields up to 87% with up to 99% substrate conversion following literature procedure (Che et al. *Org. Lett.* (2004), 6, 2405). The heterocyclic organic compound contains functional groups. In one embodiment, the heterocyclic organic compound contains at least one nitrogen atom. In another embodiment, the heterocyclic organic compound can be an aromatic compound. For example, the nitrogen atom of the heterocyclic organic compound is substituted. Non-limiting examples of substituents include a hydrogen atom, an alkyl group, an aryl group and an acyl group.

In one embodiment, the organic compound is a di(amido-substituted)-heteroarene represented by structural formula A:

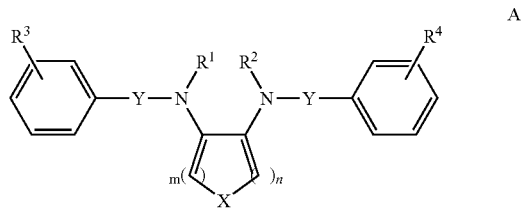

wherein positions $R^1$, $R^2$, $R^3$ and $R^4$ are each independently hydrogen, alkyl, substituted alkyl, alkenyl, substituted alkenyl, alkynyl, substituted alkynyl, phenyl, substituted phenyl, aryl, substituted aryl, heteroaryl, substituted aryl, heteroaryl, substituted heteroaryl, halo, nitro, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, phenylthio, substituted phenylthio, cyano, isocyano, substituted isocyano, carbonyl, substituted carbonyl, carboxyl, substituted carboxyl, amino, substituted amino, amido, substituted amido, sulfinyl, substituted sulfinyl, sulfonyl, substituted sulfonyl, sulfonic acid, substituted sulfonic acid, phosphonato, substituted phosphonato, phosphoramide, polyaryl, substituted polyaryl, $C_1$-$C_{20}$ cyclic, $C_1$-$C_{20}$ cyclic, heterocyclic, substituted heterocyclic, amino acid, peptide, or polypeptide group; and X is O, S or $NR^5$ where $R^5$ is independently selected from the same groups as $R^1$; n and m may be $C_1$-$C_{20}$; Y is independently selected from the same groups as $R^1$, and $SO_2$. The various R groups can be optically pure or can be stereo- and regio-isomers. In one embodiment, X is NR and Y is $SO_2$.

In another embodiment, the structure is represented by:

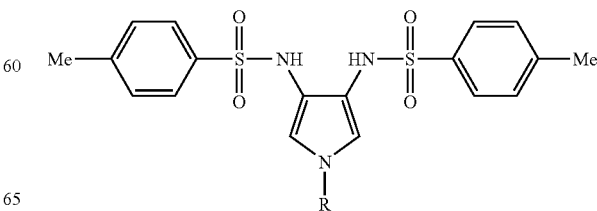

wherein R is independently hydrogen, alkyl, substituted alkyl, alkenyl, substituted alkenyl, alkynyl, substituted alkynyl, phenyl, substituted phenyl, aryl, substituted aryl, heteroaryl, substituted aryl, heteroaryl, substituted heteroaryl, halo, nitro, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, phenylthio, substituted phenylthio, cyano, isocyano, substituted isocyano, carbonyl, substituted carbonyl, carboxyl, substituted carboxyl, amino, substituted amino, amido, substituted amido, sulfinyl, substituted sulfinyl, sulfonyl, substituted sulfonyl, sulfonic acid, substituted sulfonic acid, phosphonato, substituted phosphonato, phosphoramide, polyaryl, substituted polyaryl, $C_1$-$C_{20}$ cyclic, $C_1$-$C_{20}$ cyclic, heterocyclic, substituted heterocyclic, amino acid, peptide, or polypeptide group. The R group may be optically pure or can be stereo- and regio-isomers. In one embodiment, R is an alkyl group.

In one embodiment, the 3,4-di(toluene-p-sulfonamido)-N-substituted-pyrrole can have the following structure 1:

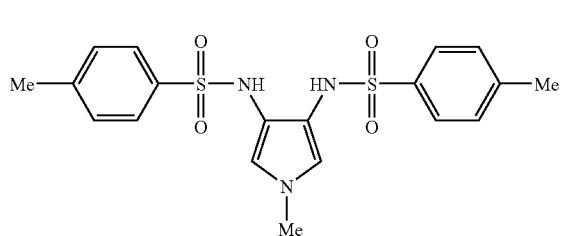

1

In another embodiment, compound 1 exhibits osteoblastogenesis modulating activity.

These and all other features, advantages, and objects of the present invention, will become evident upon review of the detailed description of the preferred embodiment and attached drawings in which:

BRIEF DESCRIPTION OF THE DRAWINGS

These and all other features, advantages, and objects of the present invention, will become evident upon review of the detailed description of the preferred embodiment and attached drawings in which.

DETAILED DESCRIPTION OF THE PREFERRED EMBODIMENTS

Figure 1:
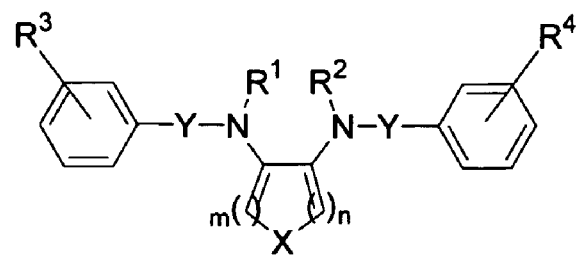
FIG. 1 illustrates the novel di(amido-substituted)heteroarenes of the present invention.
Figure 1:
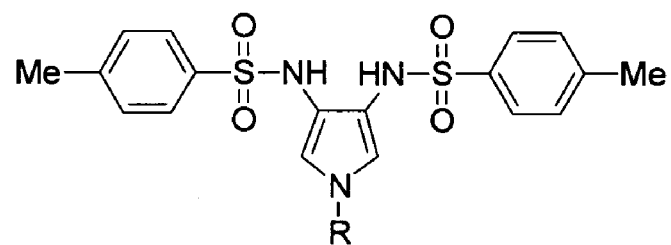
Figure 1:
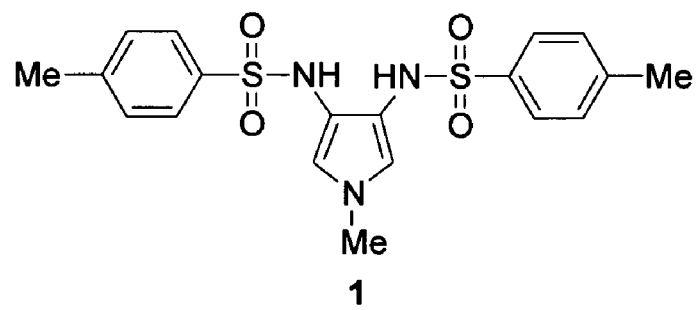

The invention relates to a method for using a unique class of di(amido-substituted)heteroarene compounds as osteoblastogenesis agents. The di(amido-substituted)heteroarene compounds show stimulatory effect on ALP activity in MC3T3-E1 (clone 4) cells at compound concentrations of 0.01 to 1 µg/mL with the presence of osteogenic medium. ALP is an early marker for osteoblast differentiation (Cheung et al, FEBS Lett (2006), 580, 121). ALP enzyme activity peaks at around day 10 and than declines at around day 14 in MC3T3-E1 (clone 4) cells under osteogenic conditions. Treatment of this compound to the MC3T3-E1 (clone 4) for 14 days resulted in a dramatic increase in ALP enzyme activity. Treatment with di(amido-substituted)heteroarene compounds (in the concentration of 0.1 and 1 µg/mL range) under osteogenic conditions for 4 days increased ALP and osterix mRNA expression. Osterix is a critical transcription factor that is essential for osteoblast differentiation (Nakashima et al, Cell (2002), 108, 17). Upregulation of ALP and osterix is indicative of the osteoblastogenic effect of this compound to stimulate osteoblast differentiation. In addition, this novel class of compounds enhanced mineralization of MC3T3-E1 (clone 4) cells with treatment for 26 days in the presence of an osteogenic medium. Furthermore, this class of compounds did not alter the proliferation of MC3T3-E1 (clone 4) cells, and exhibited low cytotoxicity as demonstrated in African green monkey Vero cells (evaluated by standard MTT-based proliferation assay; $TC_{50}$ value of no higher than 57 µM) and CCD-19L cells (vs vehicle control). The present invention describes the first application of di(amido-substituted)heteroarene compounds, a unique class of organic compounds, as osteoblastogenesis agents. Under osteogenic conditions, these compounds demonstrated potent osteoblastogenic effects in cell-based studies.

Methods of Modulating Osteoblastogenesis

The present invention provides methods for modulating osteoblastogenesis. Within certain aspects, the present invention provides modulating agents capable of enhancing osteoblastogenesis.

In one such aspect, the modulating agent comprises novel bioactive small di(amido-substituted)heteroarene compounds that could notably modulate osteoblastogenic differentiation.

In another such aspect, the present invention provides methods for enhancing osteoblast differentiation in a cell, comprising contacting the cell with an osteoblastogenesis modulating agent as described above.

Within other aspects, the present invention provides methods for enhancing osteoblast differentiation in a committed immature preosteoblast MC3T3-E1 (clone 4) cells with an osteoblastogenic modulating agent as described above, wherein the step of direct contact is performed under conditions and for sufficient time to allow the drug to mediate its osteoblastogenic actions. Within related aspects, cells can be originated from any member of the kingdom Animalia, including but not limited to MC3T3-E1 (clone 4) cells.

Pharmaceutical composition and the use of novel di(amido-substituted)heteroarene compounds for combating osteoporosis are provided herein. The pharmaceutical composition contains different synthetic di(amido-substituted) heteroarene compounds in an amount effective to exhibit osteoblastogenesis in the presence of osteogenic medium in cell-based assays.

As used herein, the phrase "di(amido-substituted)heteroarene" refers to any heteroatom containing an aromatic ring that is substituted with nitrogen containing functional groups. The compounds can be neutral, or be either overall negatively or positively charged. They can also exist as a single molecule or aggregated molecules.

As noted above, the present invention relates to compositions useful for the potent dose dependent stimulatory effect on ALP activity in MC3T3-E1 (clone 4) cells at compound concentrations in the 0.01 and 1 μg/mL range.

As used herein, the phrase "ALP activity" described herein refers to the amount of alkaline phosphatase produced by the cell.

As used herein, the term "mRNA" described herein refers to messenger ribonucleic acid.

As used herein, the term "osteogenic medium" described herein refers to complete culture medium supplemented with 400 μM ascorbic acid and 5 mM β-glycerophosphate.

As used herein, the term "MTT-based proliferation assay" described herein refers to cell proliferation assay based upon the metabolic degradation of a compound known as "3-[4,5-dimethylth-iazol-2-yl]-2,5-diphenyltetrazolium bromide."

As used herein, the term "CCD-19L cells" described herein refers to normal human lung fibroblast cell line.

As used herein, the term "control" described herein refers to 0.1% (volume/volume) of dimethylsulfoxide (DMSO) of total volume of the medium.

As used herein, the term "TTP" refers to a meso-tetrakis (tolyl)porphyrin dianion.

According to one aspect of the present invention, a method is provided for osteoporosis treatment resulting in stimulated ALP activity by administering a composition comprising an effective amount of di(amido-substituted)heteroarenes compounds in cell-based assays.

According to another aspect of the present invention, one or more di(amido-substituted)heteroarenes compounds can be provided, which can be represented by structural formula A;

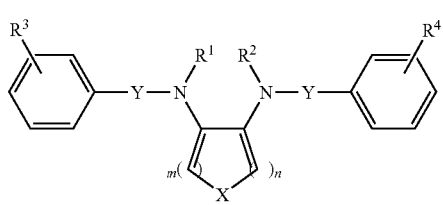

In a preferred embodiment, structural formula A is an organic compound containing an aromatic heterocycle, preferably of the N-substituted pyrrole sub-class. Representative N-substituted pyrroles include pyrrole, N-alkylpyrrole, N-arylpyrrole and N-acylpyrrole.

Herein, positions $R^1$, $R^2$, $R^3$ and $R^4$ are each independently hydrogen, alkyl, substituted alkyl, alkenyl, substituted alkenyl, alkynyl, substituted alkynyl, phenyl, substituted phenyl, aryl, substituted aryl, heteroaryl, substituted aryl, heteroaryl, substituted heteroaryl, halo, nitro, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, phenylthio, substituted phenylthio, cyano, isocyano, substituted isocyano, carbonyl, substituted carbonyl, carboxyl, substituted carboxyl, amino, substituted amino, amido, substituted amido, sulfinyl, substituted sulfinyl, sulfonyl, substituted sulfonyl, sulfonic acid, substituted sulfonic acid, phosphonato, substituted phosphonato, phosphoramide, polyaryl, substituted polyaryl, $C_1$-$C_{20}$ cyclic, $C_1$-$C_{20}$ cyclic, heterocyclic, substituted heterocyclic, amino acid, peptide, or polypeptide group; and X is O, S or $NR^5$ where $R^5$ is independently selected from the same groups as $R^1$. n and m may be $C_1$-$C_{20}$. Y is independently selected from the same groups as $R^1$, $SO_2$. The various R groups may be optically pure or can be stereo- and regio-isomers.

According to a further aspect of the present invention, a method is provided that disclose ALP as being constitutively expressed in committed immature preosteoblast MC3T3-E1 (clone 4) cells.

Figure 2:
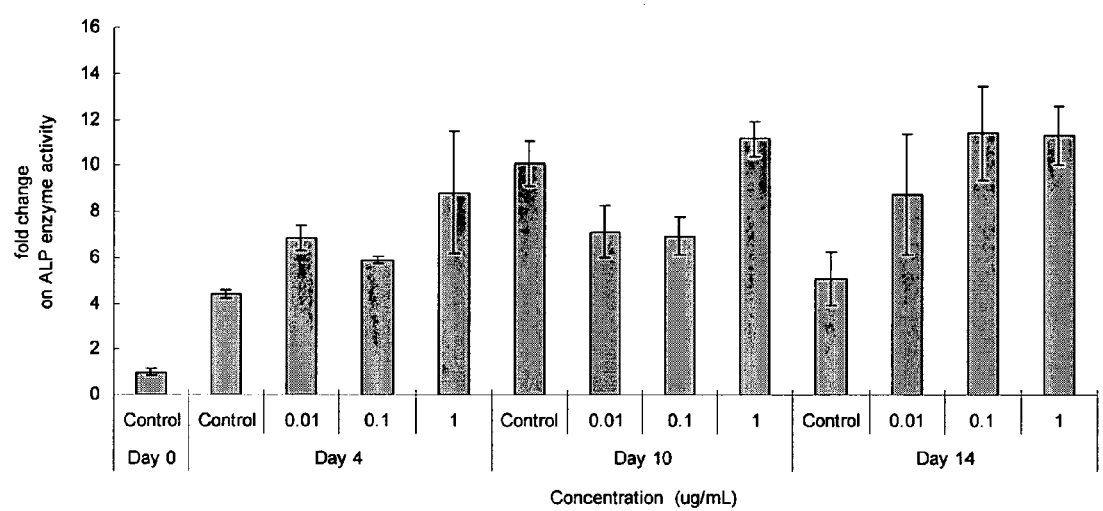
FIG. 2 illustrates the dose dependent effect on ALP enzyme activity in MC3T3-E1 (clone 4) cells, treated for 4, 10 and 14 days with compound concentrations from 0.01 to 1 µg/mL in the presence of osteogenic medium.
Figure 3:
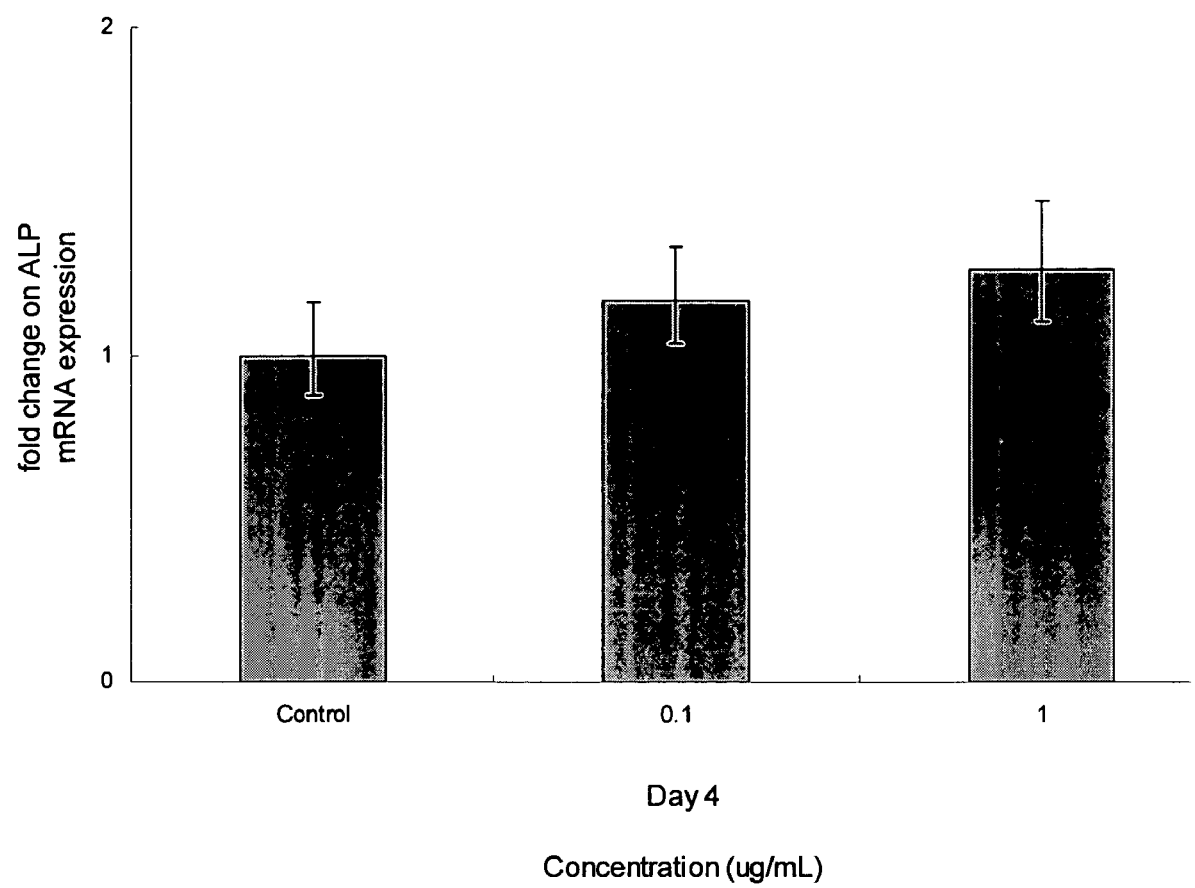
FIG. 3 illustrates the number of folds of ALP mRNA expression increased in MC3T3-E1 (clone 4) cells, treated for 4 days with compound concentrations from 0.1 to 1 µg/mL in the presence of osteogenic medium.

In one embodiment, the invention provides di(amido-substituted)heteroarene compound 1 significantly enhanced ALP activity in a dose dependent manner (in the range of 0.01 to 1 μg/mL of compound concentrations) with the presence of osteogenic medium, as shown in FIGS. 2 & 3. For one example, ALP activity was up-regulated by 2 fold after 14 days of treatment at 0.1 μg/mL compared to the control. ALP mRNA expression was also up-regulated by 16% as early as treatment of this compound at 0.1 μg/mL for 4 days. Our findings revealed that compound 1 significantly enhanced ALP activity on osteoblastic differentiation.

Figure 4:
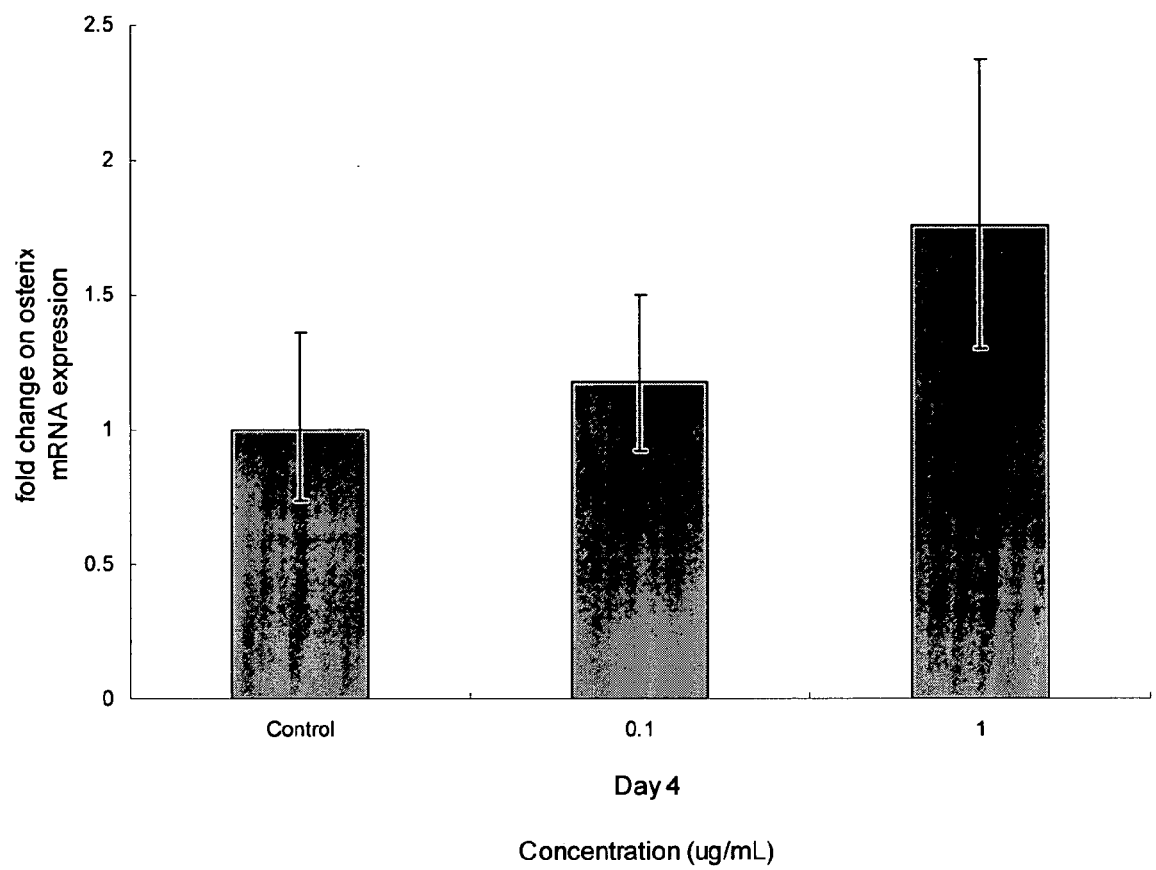
FIG. 4 illustrates the number of folds of osterix mRNA expression increased in MC3T3-E1 (clone 4) cells treated for 4 days with compound concentrations 0.1 and 1 µg/mL in the presence of osteogenic medium.

In another embodiment, the invention provides high concentrations of di(amido-substituted)heteroarene compound 1 effectively up-regulated mRNA expression of osterix in the presence of osteogenic medium (FIG. 4). Up-regulation of osteoblast lineage specific markers including ALP and osterix is indicative to the commitment of multipotential precursor cells to osteoblastic lineage.

Figure 5:
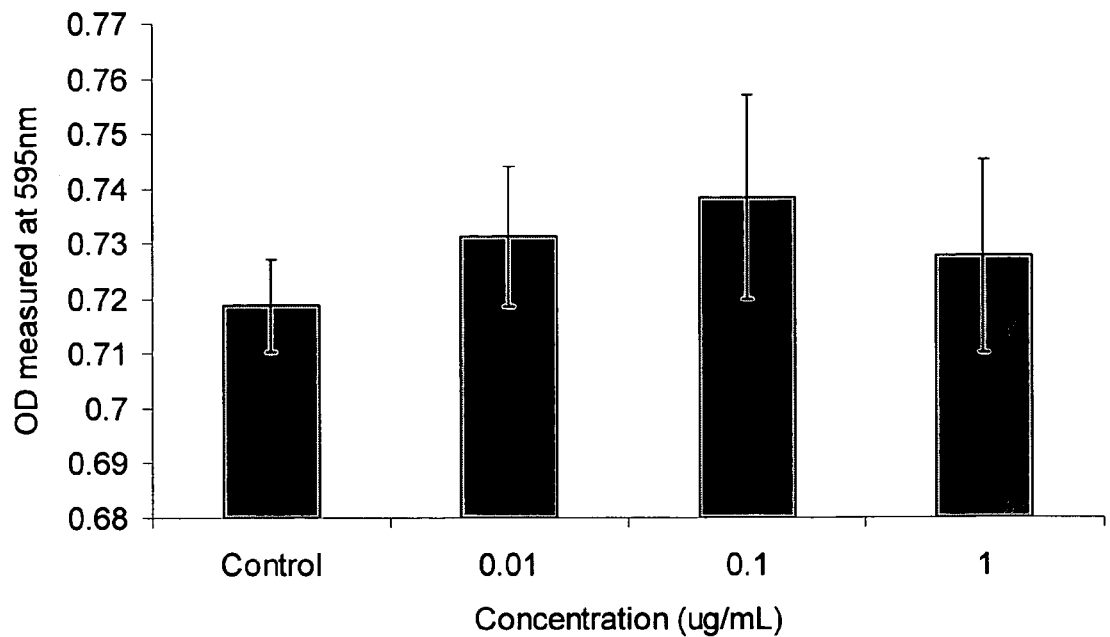
FIG. 5 illustrates the result of MTT-based proliferation assay of this di(amido-substituted)-heterocyclic organic compound in proliferation of MC3T3-E1 (clone 4) cells after treatment at compound concentrations 0.01 to 1 µg/mL for 2 days in the presence of osteogenic medium.

Importantly, the di(amido-substituted)heteroarene compound 1 did not alter MC3T3-E1 clone 4 cell proliferation evaluated in a MTT assay (FIG. 5).

Figure 6:
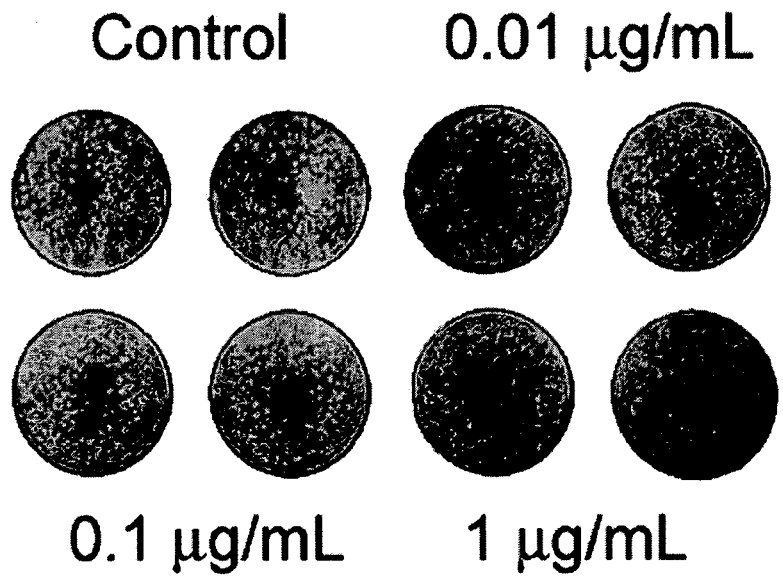
FIG. 6 illustrates the effect of this di(amido-substituted)-heterocyclic organic compound on bone mineralization of MC3T3-E1 (clone 4) cells after treatment at compound concentrations 0.01 to 1 µg/mL in the presence of osteogenic medium for 28 days.

In another embodiment, the invention provides di(amido-substituted)heteroarene compound 1 potentiated mineralization of bone nodules in MC3T3-E1 clone 4 cells (FIG. 6).

Figure 7:
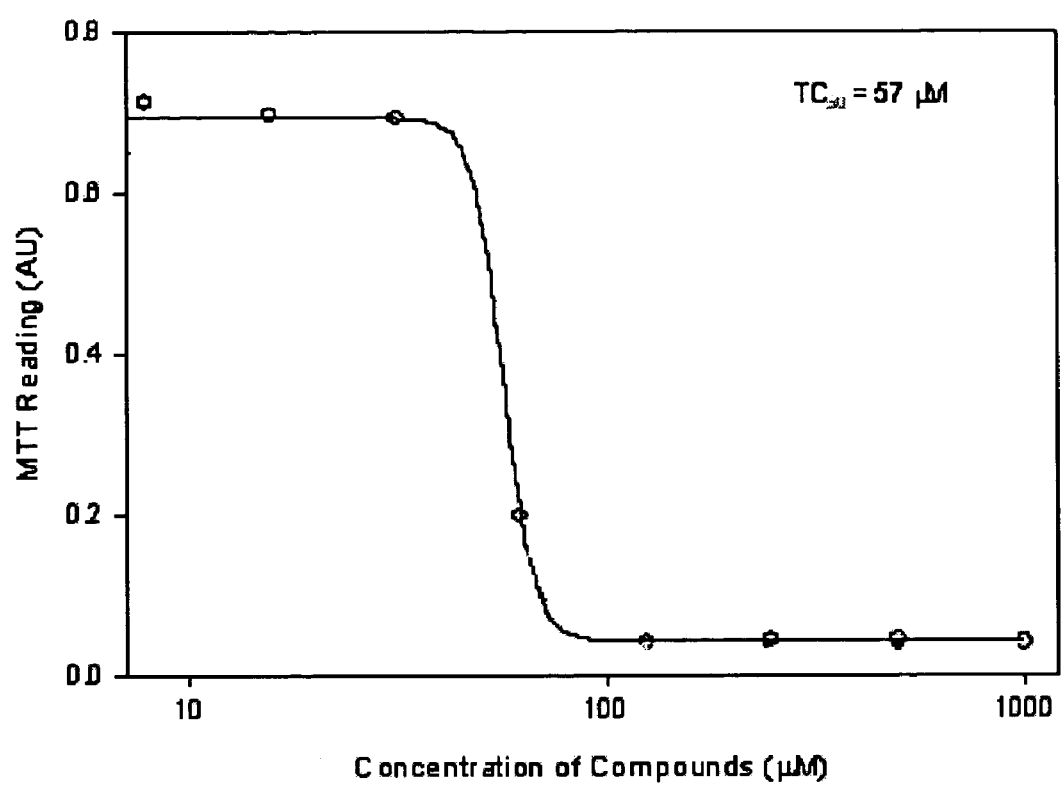
FIG. 7 illustrates the low cytotoxicity on African green monkey Vero cells evaluated by standard MTT-based proliferation assay, with a $TC_{50}$ value of no higher than 57 µM and low cytotoxicity on CCD-19L cells (vs. vehicle control) exhibited by the novel di(amido-substituted)heteroarenes of this invention.
Figure 8:
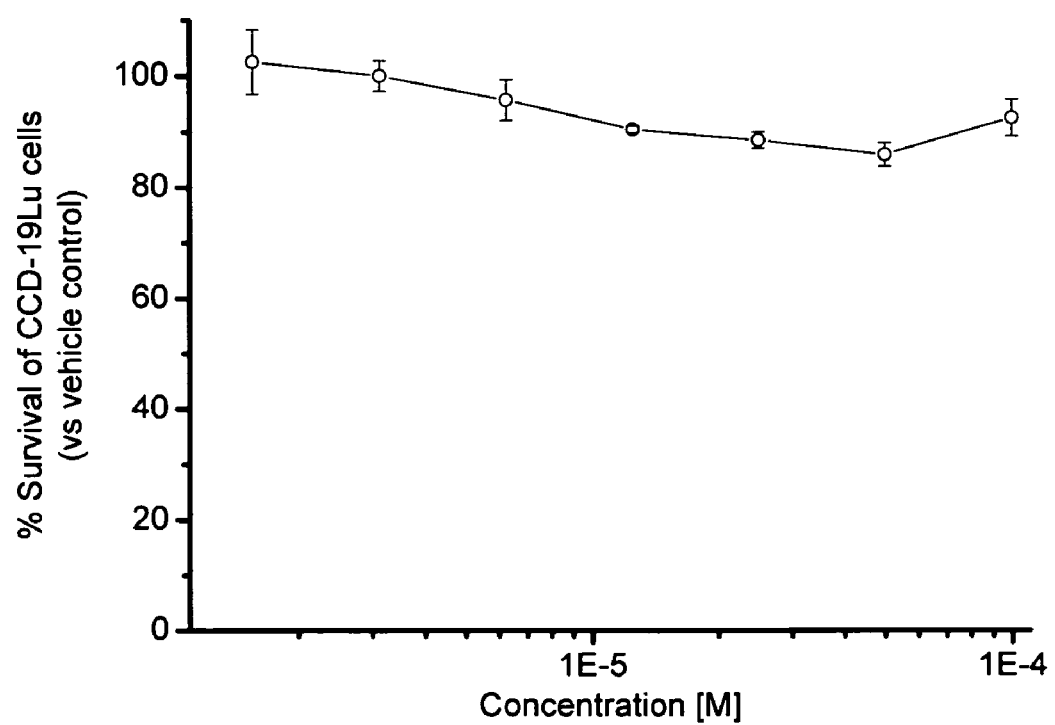
FIG. 8 illustrates the low cytotoxicity on CCD-19L cells (vs vehicle control) exhibited by the novel di(amido-substituted)heteroarenes of this invention.

The di(amido-substituted)heteroarene compound 1, of the present invention shows low cytotoxicity in African green monkey Vero cells evaluated by standard MTT assay ($TC_{50}$ value of no higher than 57 μM, FIG. 7), and low cytotoxicity on CCD-19L cells (vs vehicle control, see FIG. 8).

Synthesis of Di(amido-substituted)heteroarene Compounds

In general, the di(amido-substituted)heteroarene compounds of this invention can be prepared by reacting the appropriate heteroarene substrate with the desired nitrogen source at 40° C. under sondicating conditions and an inert argon gas atmosphere for 2 h.

In this invention, the compositions described herein are di(amido-substituted)heteroarene compounds having the following structure A:

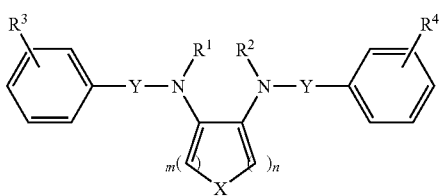

An exemplary synthetic di(amido-substituted)heteroarene compound of formula A is given below:

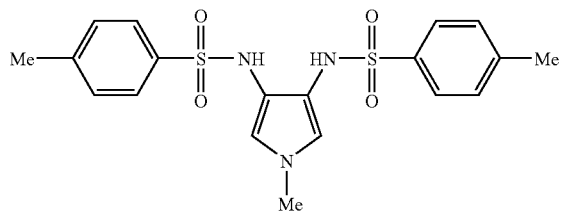

The di(amido-substituted)heteroarene compounds can be prepared according to the literature method. High purity di(amido-substituted)heteroarene compounds were obtained by flash column chromatography. The di(amido-substituted) heteroarene compounds were characterized by $^1$H and $^{13}$C NMR spectroscopy, high resolution mass spectroscopy (EI), IR spectroscopy, and elemental analysis.

EXAMPLES

The following examples are set forth to assist in understanding the invention and should not be construed as specifically limiting the invention described and claimed herein.

Materials. All reactions were performed under an argon atmosphere. [RuII(TTP)(CO)] was prepared according to known literature procedures. Unless specified, all reagents and starting materials were purchased from commercial sources and used as received. Organic solvents were purified following standard literature procedures, and double distilled deionized water was used throughout the experiments. 4 Å Molecular sieves were dried at 300° C. and cooled under reduced pressure prior to use.

Cell culture. MC3T3-E1 (clone 4) cells (American Tissue Culture Collection, Manassas, Va., U.S.A.) were maintained in complete growth medium, i.e., alpha-MEM supplemented with 100 U/mL penicillin, 100 μg/mL streptomycin, and 10% heat-inactivated fetal bovine serum (JRH Biosciences, Lenexa, Kans., U.S.A. Ascorbic acid (AsA) and β-glycerophosphate (β-GP) were purchased from Sigma-Aldrich Co. (St. Louis, Mass., U.S.A.). For the screening of osteoblastogenesis-inducing compounds, cells were plated in 24-well plates in complete growth medium at $5 \times 10^4$ cells/cm$^2$ and after overnight incubation, potential osteoblastogenesis modulating agents were added at 3 different concentrations, each with 10 fold difference. For osteoblastogenesis-promoting compounds, cells were cultured with complete growth medium supplemented with osteogenic medium containing 400 μM AsA and 5 mM β-GP. In both cases, fresh complete growth medium and candidate small molecules were replenished every 2-3 days. After 4 days, cells were collected for intracellular ALP and protein measurement; total RNA was also prepared for gene expression analysis.

ALP assay. ALP activity was measured as p-nitrophenol produced from the hydrolysis of p-nitrophenyl phosphate (PNPP). In brief, cells were washed with ice-cold PBS, lysed with 50 mM Tris, pH 7.4, and 0.1% Triton-X100, and incubated with 2-amino-2-methyl-1-propanol buffer (0.5 M, pH 10.4) containing 10 mM PNPP at 37° C. for 15-30 min. The reaction was stopped by the addition of NaOH (final concentration, 0.5 M) and the absorbance was measured at 410 nm. Enzyme activity was normalized to the protein content determined using Protein Assay Kit (Bio-Rad). Experiments were performed in triplicate wells and data shown are representative of two independent experiments.

Real-time quantitative reverse transcription (RT) PCR. Total RNA was isolated from cultured cells using TRI Reagent (Molecular Research Center, Inc., Cincinnati, Ohio, U.S.A.). First-strand cDNA was synthesized in a 12.5-μl reaction from 1.5 μg total RNA by RT with M-MLV reverse transcriptase (Promega Co., Madison, Mich., U.S.A.) using 250 ng random hexamers at 37° C. for 60 min. The cDNA was subsequently diluted to 100 μL in diethylpyrocarbonate-treated water. ALP and osterix mRNA expression was determined by RT followed by real-time TaqMan PCR analysis. Oligonucleotide primers and TaqMan probes for ALP, osterix and 18S ribosomal RNA (18S) internal control, and PCR reagents were obtained from Applied Biosystems Inc. (Foster City, Calif., U.S.A.). In a 20-μL PCR, 4.5 μL diluted cDNA was amplified in a 7000 sequence detector (Applied Biosystems), using the 2× Universal master mix, 25 nM primers, and 100 nM probe (VIC-TAMRA labeled) for the 18S, and 300 nM primers and 200 nM probe (FAM-TAMRA labeled) for ALP/osterix. Cycling conditions were 95° C. for 15 seconds, 60° C. for 1 minute for 40 cycles. All PCR reactions were performed in triplicate and data obtained were analyzed using the comparative CT method (Applied Biosystems) with ALP/osterix signals normalized to 18S signal for each sample.

Cell proliferation assay. Cell proliferation studies were performed as previously described using MTT-based (GE Healthcare, Piscataway, N.J., USA) cell proliferation assays (Cheung et al/, FEBS Lett (2006), 580, 121). After treatment with potential osteoblastogenesis modulating agents for 2 days, MTT was added at a final concentration of 0.5 mg/ml for 3 h, cells were solubilized with isopropanol containing 0.1% sodium dodecyl sulfate and 0.04 N hydrochloric acid, and the absorbance measured at 570 nm. All experiments were repeated three times.

Cytotoxicity assay. Vero cells, an African green monkey cell line were purchased from American Type Culture Collection (ATCC) and Cell Proliferation Kit I MTT (3-[4,5-dimethylth-iazol-2-yl]-2,5-diphenyltetrazolium bromide) assay was purchased from Roche. Normal human lung fibroblast cell line (CCD-19Lu) was obtained commercially from ATCC. CCD-19Lu cells were maintained in a minimum essential medium with Earle's balanced salts (MEM). The media were supplemented with L-glutamine (2 mM), fetal bovine serum (10%), penicillin (100 U/mL) and streptomycin (100 μg/mL). Cultures were incubated at 37° C. in a 5% CO$_2$/95% air humidified atmosphere. Cell culture flasks and 96-well microtitre plates were purchased from Nalge Nunc Int. Culture medium, other medium constituents and phosphate buffered saline (PBS) were from Gibco BRL.

Instrumentation. Mass spectra (including fast atom bombardment (FAB) mass spectra), determined at an ionizing voltage of 20 eV, were recorded on a Finnigan MAT95 mass spectrometer. 1H and 13C NMR spectra were measured at 400, 300, 100 and 75 MHz, respectively, on Bruker DPX-300 or DPX-400 NMR spectrometers with tetramethylsilane (TMS) as the internal standard and with chemical shifts (ppm) recorded relative to TMS. Elemental analyses were carried out by the Institute of Chemistry, the Chinese Academy of Sciences (Beijing, P. R. China).

Example 1

Procedure for Direct Amidation of Unfunctionalized Hetereoarenes with PhI=NTs

The invention provides a method for using a unique class of di(amido-substituted)heteroarene compounds as osteoblastogenesis agents. Example 1 describes the preparation of di(amido-substituted)heteroarene compounds by reacting the appropriate heteroarene substrate with the desired nitrogen source at 40° C. under sondicating conditions and an inert argon gas atmosphere for 2 h.

Typical conditions employ 1 equiv of hetereoarene substrate, PhI=NTs (5 equiv), catalyst (10 mol %), 4 Å molecular sieves (amount used equivalent by mass to amount of PhI=NTs) and $CH_2Cl_2$ (10 mL) in a dry Schlenk flask under an argon atmosphere. The reaction mixture was placed in a sondicating bath at 40° C. for 2 h. On cooling to room temperature, the mixture was filtered, concentrated in situ and purified by silica gel column chromatography (petroleum ether/EtOAc as eluent) to give the title compound.

All the target di(amido-substituted)heteroarene compounds were characterized by 1H and 13C NMR spectroscopy, and HRMS spectrometry. 1:

1H NMR (400 MHz, CDCl3): δ 7.87 (s, 2H), 7.84 (d, 4H, J=8.2 Hz), 7.33 (d, 4H, J=8.1 Hz), 3.07 (s, 3H), 2.43 (s, 6H); 13C NMR (100 MHz, CDCl3): δ 126.1, 144.4, 137.0, 129.7, 129.4, 127.3, 26.9, 21.7; HRMS (EI): m/z Calcd. for $C_{19}H_{21}N_3S_2O_4$: 419.0973. Found: 419.0885.

Example 2

Assessment of Osteoblastic Cell Differentiation through Measurement of ALP Activity Example 2 describes the procedures employed to examine the dose dependent stimulatory effects of di(amido-substituted)heteroarene compounds on committed immature preosteoblast MC3T3-E1 (clone 4) cells and the results of these studies.

MC3T3-E1 (clone 4) cells were cultured for 4, 10, and 14 days with the presence of VCM supplemented with different concentrations (range from 0.01 to 1 μg/mL) of di(amido-substituted)heteroarene compounds. Control was performed by treatment of MC3T3-E1 clone 4 cells with equal volume of solvent. After 0, 4, 10 and 14 days, cells were collected for ALP enzyme activity measurement. ALP activity was measured as p-nitrophenol produced from the hydrolysis of p-nitrophenyl phosphate (PNPP). In brief, cells were washed with ice-cold PBS, lysed with 50 mM Tris, pH 7.4, and 0.1% Triton-X100, and incubated with 2-amino-2-methyl-1-propanol buffer (0.5 M, pH 10.4) containing 10 mM PNPP at 37° C. for 15-30 min. The reaction was stopped by the addition of NaOH (final concentration, 0.5 M) and the absorbance measured at 410 nm. Enzyme activity was normalized to the protein content determined using Protein Assay Kit (Bio-Rad). Day 0 was designated as 1 and the number of folds of ALP activity after day 4, 10 and 14 was compared with day 0. Experiments were performed in triplicate wells and data shown are representative of two independent experiments.

Di(amido-substituted)heteroarene compound 1 in the presence of the osteogenic medium, significantly enhanced ALP enzyme activity in a dose-dependent manner as shown in FIG. 2. ALP is an early marker for osteoblast differentiation. In the control situation, ALP enzyme activity peaked at around day 10 and then declined at around day 14 in MC3T3-E1 (clone 4) cells under osteogenic conditions. Treatment of this compound to the MC3T3-E1 (clone 4) cells for 14 days resulted in a dramatic increase in ALP enzyme activity. ALP activity was up-regulated by 2 fold at day 14, compared to the control cells. The present invention describes the first application of di(amido-substituted)heteroarene compounds, a unique class of organic compounds, as osteoblastogenesis agents and under osteogenic conditions, demonstrated potent dose dependent effects on ALP enzyme activity in cell-based studies.

Example 3

Total RNA Extraction and ALP Gene Expression Analysis by Real Time Quantitative PCR Example 3 describes the procedures employed to examine the stimulatory effects of di(amido-substituted)heteroarene compounds on committed immature preosteoblast MC3T3-E1 (clone 4) cells and the results of these studies.

MC3T3-E1 (clone 4) cells were cultured for 4 days, and total RNA was extracted. Control was performed by treatment of MC3T3-E1 (clone 4) cells with equal volume of solvent and its ALP mRNA expression was designated as 1. Expression level of osterix expression in MC3T3-E1 (clone 4) cells was determined using Real-Time TaqMan polymerase chain reaction (PCR). The mRNA expression level of ALP was normalized to the 18S expression. Data are presented as the relative expression level of ALP in MC3T3-E1 (clone 4) cells treated with di(amido-substituted)heteroarene compound 1 versus solvent control. Results (mean ±S.D.) are representative of two independent experiments, each performed in triplicates.

Di(amido-substituted)heteroarene compound 1 of this invention enhanced ALP mRNA expression in MC3T3-E1 (clone 4) cells at concentration 0.1 and 1 μg/mL (FIG. 3). The present invention describes the first application of di(amido-substituted)heteroarene compounds, a unique class of organic compounds, as osteoblastogenesis agents and under osteogenic conditions, demonstrated potent effects on ALP mRNA expression in cell-based studies.

Example 4

Total RNA Extraction and Gene Expression Analysis by Real Time Quantitative PCR

Example 4 describes the procedures employed to examine the stimulatory effects of di(amido-substituted)heteroarene compounds on committed immature preosteoblast MC3T3-E1 (clone 4) cells and the results of these studies.

MC3T3-E1 (clone 4) cells were cultured for 4 days, and total RNA was extracted. Control was performed by treatment of MC3T3-E1 (clone 4) cells with equal volume of solvent and its osterix mRNA expression was designated as 1. Expression level of osterix expression in MC3T3-E1 (clone 4) cells was determined using Real-Time TaqMan PCR. The mRNA expression level of osterix was normalized to the 18S expression. Data are presented as the relative expression level of osterix in MC3T3-E1 (clone 4) cells treated with di(amido-substituted)heteroarene compound 1 versus solvent treatment. Results (mean ±S.D.) are representative of two independent experiments, each performed in triplicates.

Di(amido-substituted)heteroarene compound 1 of this invention enhanced osterix mRNA expression in MC3T3-E1 (clone 4) cells at concentration 1 μg/mL (FIG. 4). The present invention describes the first application of di(amido-substituted)heteroarene compounds, a unique class of organic compounds can enhance osterix mRNA expression in cell-based studies and highlight the effect of the compound on gene activation of osterix, an important transcriptional factor required for differentiating mesenchymal stem cells to osteoblast lineage.

Example 5

Cell Proliferation Assays

Example 5 describes the procedures employed to examine the proliferative effect of di(amido-substituted)heteroarene compounds on MC3T3-E1 (clone 4) cells evaluated by MTT assay and the results of these studies.

Cell proliferation studies were performed as previously described using MTT (GE Healthcare, Piscataway, N.J., USA) assays (Cheung et al, FEBS Lett (2006), 580, 121). After treatment with the candidate compounds (concentrations 0.01 to 1 μg/mL) for 2 days, MTT was added at a final concentration of 0.5 mg/ml for 3 h, cells were solubilized with isopropanol containing 0.1% sodium dodecyl sulfate and 0.04 N hydrochloric acid, and the absorbance measured at 570 nm. All experiments were repeated three times.

Novel class of compounds did not alter cellular proliferation of MC3T3-E1 clone 4 cells (as shown in FIG. 5).

Example 6

Bone Nodule Formation and Mineralization in MC3T3 E1 Clone 4 Cells

Example 6 describes the procedures employed to examine the effect of di(amido-substituted)heteroarene compounds on bone nodule formation evaluated by Alizarin red stain and the results of these studies.

Cells were washed twice with ice-cold PBS and then fixed in ice-cold fixative (10% formalin in PBS) for 15 min. After washed with deionized water, fixed cells were stained with with 1% alizarin S solution, pH 4.2 for 15 min and then were washed thoroughly with deionized water. Mineralized matrix was then detected.

Treatment of cells with this novel class of compounds (from 0.01 to 1 μg/mL) for 26 days under osteogenic conditions resulted in increased mineralization of bone-like nodules in MC3T3-E1 (clone 4) cells.

Example 7

Cytotoxicity Studies of Di(amido-substituted)heteroarene Compounds toward African Green Monkey Vero Cell Line Example 7 describes the procedures employed to examine the cytotoxicity of di(amido-substituted)heteroarene compounds on African green monkey Vero cells evaluated by standard MTT assay and the results of these studies.

The cytotoxicity of selected compounds was determined by MTT according to manufacturer's (Roche) instructions. The experiment (cell viability using MTT as an indicator) was carried out in triplicates. The TC50 (on Vero cells, an African green monkey cell line) is ca. 50 μM, it is concluded that these compounds may be useful for osteoblastogenesis development.

Di(amido-substituted)heteroarene compound 1 of this invention exhibited low cytotoxicity on African green monkey Vero cells evaluated by standard MTT assay. For 1, a TC50 value of 57 μM was observed (FIG. 7), as shown in FIG. 7.

Example 7 describes the procedures employed to examine the cytotoxicity of di(amido-substituted)heteroarene compounds on African green monkey Vero cells evaluated by standard MTT assay and the results of these studies.

Example 8

Cytotoxicity Studies of Di(amido-substituted)heteroarene Compounds toward CCD-19L (vs Vehicle Control) Cell Line Example 8 describes the procedures employed to examine the cytotoxicity of di(amido-substituted)heteroarene compounds on CCD-19L (vs. vehicle control), and the results of these studies.

Assays on cytotoxic effects were conducted in 96-well flat-bottomed microtitre plates. The supplemented culture medium (100 μL) with cells ($3 \times 10^5$ cells/mL) was added into each well and was incubated (37° C., 5% $CO_2$/95% air) for 24 h. All the media were removed and serum free supplemented medium (100 μL) was added into each well. After further incubation for 24 h, the di(amido-substituted)heteroarene compounds dissolved in the culture medium (100 μL+<1% DMSO) were added into a set of wells. After mixing, the compound-containing media (100 μL) were drawn and added to another set of wells. Such processes were repeated to provide a set of two-fold dilution series. Controlled wells only contained 100 μL of supplemented media. Microtitre plates were incubated at 37° C. in a 5% $CO_2$/95% air humidified atmosphere for further 72 h. All the cytotoxicity assays were run in parallel with a negative control (i.e., vehicle control) and a positive control using cisplatin as cytotoxic agent. Assessment of the cytotoxicity was carried out using a modified method of Mosmann based MTT assay (Mosmann, *J. Immunol. Methods* (1983), 65, 55). At the end of each incubation period, 10 μL of MTT solution were added into each well and the cultures were further incubated for 4 h at 37° C. in a 5% $CO_2$/95% air humidified atmosphere. This was followed by 100 μL of the solubilization solution was added into the wells to lyse the cells and solubilize the formazan complex formed. The microtitre plates were maintained in a dark, humidified chamber overnight. The formation of formazan was measured with a microtitre plate reader at 550 nm and the percentages of cell survival were determined. The cytotoxicity was evaluated based on the percentage cell survival in a dose dependent manner relative to the negative control (FIG. 8).

The above description and examples are only illustrative of preferred embodiments which achieve the objects, features, and advantages of the present invention, and it is not intended that the present invention be limited thereto. Any modifications of the present invention which come within the spirit and scope of the following claims is considered part of the present invention.

REFERENCES

The disclosures of the following publications are hereby incorporated herein by reference in their entirety:
1. Chestnut in III: Osteoporosis: A world-wide problem, *Osteoporosis* 1990: Denmark, Osteopress ApS (1990), 33.
2. Lane, Epidemiology, etiology, and diagnosis of osteoporosis. *Am J Obstet Gynecol* (2006), 194, S3.

3. Che et al., Ruthenium(II) porphyrin-catalyzed amidation of aromatic heterocycles. *Org. Lett.* (2004), 6, 2405.
4. Che et al., Unusual metalloporphycenes. First syntheses of carbonyl- and dioxo-containing osmium and ruthenium tetrapropylporphycene complexes. *Inorg. Chem.* (1992), 31, 2670.
5. Mosmann, Rapid Colorimetric Assay for Cellular Growth and Survival: Application to Proliferation and Cytotoxicity Assays. *J. Immunol. Methods* (1983), 65, 55.
6. Nakashima et al, The novel zinc finger-containing transcription factor osterix is required for osteoblast differentiation and bone formation. *Cell* (2002), 108, 17.
7. Cheung et al., Dimethyl sulfoxide as an inducer of differentiation in preosteoblast MC3T3-E1 cells. *FEBS. Lett.* (2006), 580, 121.

What is claimed is:

1. A method for the treatment of osteoporosis comprising contacting osteoblastic cells with an effective amount of one or more di(amido-substituted) heteroarene compounds having the structural formula A in a pharmaceutically acceptable vehicle:

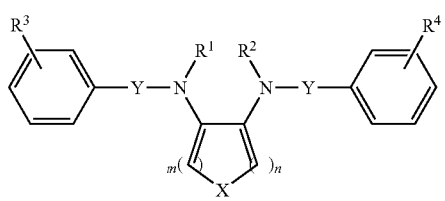

wherein positions $R^1$, $R^2$, $R^3$ and $R^4$ are each independently hydrogen, alkyl, substituted alkyl, alkenyl, substituted alkenyl, alkynyl, substituted alkynyl, phenyl, substituted phenyl, aryl, substituted aryl, heteroaryl, substituted aryl, heteroaryl, substituted heteroaryl, halo, nitro, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, phenylthio, substituted phenylthio, cyano, isocyano, substituted isacyano, carbonyl, substituted carbonyl, carboxyl, substituted carboxyl, amino, substituted amino, amido, substituted amido, sulfinyl, substituted sulfinyl, sulfonyl, substituted sulfonyl, sulfonic acid, substituted sulfonic acid, phosphonato, substituted phosphonato, phosphoramide, polyaryl, substituted polyaryl, $C_1$-$C_{20}$ cyclic, $C_1$-$C_{20}$ cyclic, heterocyclic, substituted heterocyclic, amino acid, peptide, or polypeptide group; X is O, 8 or $NR^5$ where $R^5$ is independently selected from the same groups as $R^1$; n and m may be $C_1$-$C_{20}$; Y is independently selected from the same groups as $R_1$ or is $SO_2$ and wherein $R^1$ through $R^4$ may be optically pure or a stereo- or region-isomer.

2. The method according to claim 1, wherein the di(amido substituted) heteroarene compounds induce osteoblastogenesis in preosteoblastic cells.

3. The method of claim 1, wherein the osteoblastic cells are mammalian cells.

4. The method according to claim 1, wherein the osteoblastic cells are a preosteoblast MC3T3-E1 clone 4 cells.

5. The method according to claim 1, wherein the di(amido-substituted) heteroarene compounds cause a dose-dependent stimulation in committed immature preosteoblast MC3T3-E1 clone 4 cells.

6. The method according to claim 4, wherein the di(amido-substituted) heteroarene compound stimulates differentiation of immature preosteoblast MC3T3-E1 (clone 4) cells to mature osteoblasts.

7. The method according to claim 5, wherein the di(amido-substituted) heteroarene compounds stimulates osterix mRNA expression in committed immature preosteoblast MC3T3-E1 (clone 4) cells.

8. The method according to claim 1, wherein the di(amido-substituted) heteroarene compounds lack cytotoxicity in committed immature preosteoblast MC3T3-E1 (clone 4) cells at 1 μg/ml.

9. The method according to claim 1, wherein the di(amido-substituted) heteroarene compounds stimulate formation of mineralized of bone-like nodules in MC3T3-E1 (clone 4) cells.

10. A di(amido-substituted)-heteroarene compound having structure A:

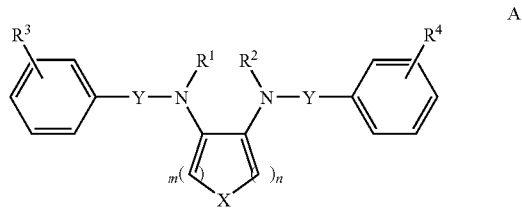

wherein positions $R^1$, $R^2$, $R^3$ and $R^4$ are each independently hydrogen, alkyl, substituted alkyl, alkenyl, substituted alkenyl, alkynyl, substituted alkynyl, phenyl, substituted phenyl, aryl, substituted aryl, heteroaryl, substituted aryl, heteroaryl, substituted heteroaryl, halo, nitro, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, phenylthio, substituted phenylthio, cyano, isocyano, substituted isocyano, carbonyl, substituted carbonyl, carboxyl, substituted carboxyl, amino, substituted amino, amido, substituted amido, sulfinyl, substituted sulfinyl, sulfonyl, substituted sulfonyl, sulfonic acid, substituted sulfonic acid, phosphonato, substituted phosphonato, phosphoramide, polyaryl, substituted polyaryl, $C_1$-$C_{20}$ cyclic, $C_1$-$C_{20}$ cyclic, heterocyclic, substituted heterocyclic, amino acid, peptide, or polypeptide group; X is O, S or $NR^5$ where $R^5$ is independently selected from the same groups as $R^1$; n and m may be $C_1$-$C_{20}$; Y is independently selected from the same groups as $R^1$ or is $SO_2$ and wherein $R^1$ through $R^4$ may be optically pure or a stereo- or region-isomer.

11. The compound according to claim 10, wherein X is NR and Y is $SO_2$.

12. A compound having the following structure:

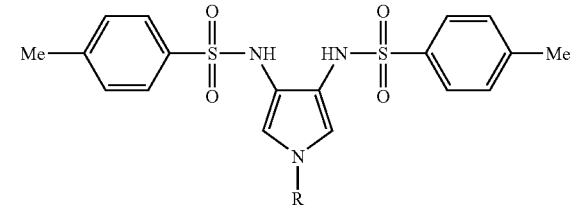

wherein R is independently hydrogen, alkyl, substituted alkyl, alkenyl, substituted alkenyl, alkynyl, substituted alkynyl, phenyl, substituted phenyl, aryl, substituted aryl, heteroaryl, substituted aryl, heteroaryl, substituted heteroaryl, halo, nitro, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, phenylthio, substituted phenylthio, cyano, isocyano, substituted isocyano, carbonyl, substituted carbonyl, carboxyl, substituted carboxyl, amino, substituted amino, amido, substituted amido, sulfinyl, substituted sulfinyl, sulfonyl, substituted sulfonyl, sulfonic acid, substituted sulfonic acid, phosphonato, substituted phosphonato, phosphoramide, polyaryl, substituted polyaryl, $C_1$-$C_{20}$ cyclic, $C_1$-$C_{20}$ cyclic, heterocyclic, substituted heterocyclic, amino acid, peptide, or polypeptide group, and wherein R may be optically pure or a stereo- and region-isomer.

13. The compound according to claim 12, wherein R is an alkyl group.

14. The compound according to claim 13, wherein the 3,4-di(toluene-psulfonamido)-N-substituted-pyrrole has the structure 1:

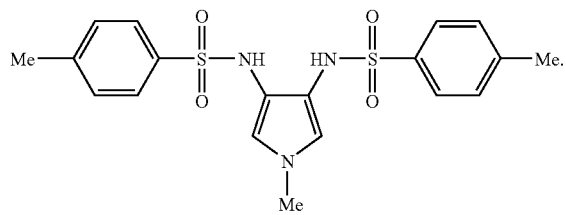

15. The compound according to claim 14, wherein the compound exhibits osteoblastogenesis activity when contacted with a cell capable of undergoing osteogenesis.

16. A method for inducing or modulating osteogenesis in cells capable of undergoing osteogenesis, comprising contacting the cells with an effective osteogenesis inducing or modulating amount of a compound according to claim 12, under conditions wherein the cells absorb the compound.

17. A method for inducing or modulating osteogenesis in cells capable of undergoing osteogenesis, comprising contacting the cells with an effective osteogenesis inducing or modulating amount of a compound according to claim 14, under conditions wherein the cells absorb the compound.

18. A method for inducing or modulating osteogenesis in cells capable of undergoing osteogenesis, comprising contacting the cells with an effective osteogenesis inducing or modulating amount of a compound according to claim 10, under conditions wherein the cells absorb the compound.

19. A method for the treatment of osteoporosis compound contacting osteoblastic cells in a patient with effective amount of the composition of compound 10.

20. A method for the treatment of osteoporosis compound contacting osteoblastic cells in a patient with effective amount of the composition of compound 12.

21. A method for the treatment of osteoporosis compound contacting osteoblastic cells in a patient with effective amount of the composition of compound 14.

* * * * *